(12) United States Patent
Naik et al.

(10) Patent No.: US 8,507,590 B2
(45) Date of Patent: Aug. 13, 2013

(54) FLUORESCENT BRIGHTENERS, METHODS OF PREPARATION THEREOF, FLUORESCENT BRIGHTENER COMPOSITIONS, AND METHODS OF PREPARATION AND USES THEREOF

(75) Inventors: Shantaram Narayan Naik, Bangalore (IN); Adil Minoo Dhalla, Dadar Mumbai (IN); Yogendrasinh Bharatsinh Chauhan, Gujarat (IN)

(73) Assignee: Sabic Innovative Plastics IP B.V. (NL)

( * ) Notice: Subject to any disclaimer, the term of this patent is extended or adjusted under 35 U.S.C. 154(b) by 0 days.

(21) Appl. No.: 13/452,356

(22) Filed: Apr. 20, 2012

(65) Prior Publication Data

US 2012/0203001 A1 Aug. 9, 2012

Related U.S. Application Data

(62) Division of application No. 12/561,764, filed on Sep. 17, 2009, now Pat. No. 8,183,310, and a division of application No. 11/285,336, filed on Nov. 21, 2005, now Pat. No. 7,608,715.

(51) Int. Cl.
*C07D 221/06* (2006.01)

(52) U.S. Cl.
USPC .............................. 524/79; 546/98

(58) Field of Classification Search
USPC ..................................... 564/79, 98
See application file for complete search history.

(56) References Cited

U.S. PATENT DOCUMENTS

| | | | |
|---|---|---|---|
| 3,310,564 A | 3/1967 | Kasai | |
| 4,814,453 A | 3/1989 | Schinzel et al. | |
| 4,814,456 A | 3/1989 | Michael | |
| 5,310,940 A | 5/1994 | Goda et al. | |
| 5,817,448 A | 10/1998 | Hayashi et al. | |
| 6,492,032 B1 | 12/2002 | Irick, Jr. et al. | |
| 7,608,715 B2 | 10/2009 | Naik et al. | |
| 2005/0171252 A1 | 8/2005 | Schambony et al. | |
| 2007/0100033 A1 | 5/2007 | Schambony et al. | |
| 2007/0117887 A1 | 5/2007 | Naik et al. | |

FOREIGN PATENT DOCUMENTS

| | | |
|---|---|---|
| GB | 2183667 A | 6/1987 |
| JP | 56167383 A | 12/1981 |
| JP | 59114546 A | 7/1984 |
| JP | 03232858 A | 10/1991 |
| WO | 2005047265 A1 | 5/2005 |
| WO | 2005102250 A1 | 11/2005 |
| WO | 2007014902 A2 | 2/2007 |

OTHER PUBLICATIONS

Application No. WO2007014902; Publication Date: Feb. 8, 2007; Abstract Only; 1 page.
Bojinov V et al. ; "A New Method for Synthesis of 4-allyloxy-1,8-naphthalimide Derivatives for Use as Fluorescent Brighteners"; Dyes and Pigments, Elsevier Applied Science Publishers, Barking, GB; vol. 51 No. 1; Oct. 1, 2001; pp. 57-61.
Cao Haishi et al.;"Matrix Screening of Substituted N-aryl-1,8-naphthalimides Reveals New Dual Fluorescent Dyes and Unusually Bright Pyridine Derivatives", J. Org. Chem.; Journal of Organic Chemistry; vol. 70, No. 13; Jun. 24, 2005; pp. 4929-4934.
Database Registry (Online); Chemical Abstracts Service, Colombus, Ohio, US; Oct. 17, 2001 XP002481508.
Grabchev I et al.; "Copoylyrmization and Photostabilization of Methylmethacrylate with 1,8-Naphthalimide Fluorescent Brighteners"; Journal of Photochemistry, and Photobiology, A; Chemistry, Elsevier Sequoia, Lausanne, CH; vol. 142, No. 1; Jan. 1, 2001; pp. 73-78.
International Search Report; International Application No. PCT/US2006/044998; International Filling Date: Nov. 20, 2006 Date of Mailing: Jun. 9, 2008; 9 pages.
Japanese Patent No. 03232858; Publication Date: Oct. 16, 1991; Abstract Only; 1 page.

(Continued)

*Primary Examiner* — Kriellion Sanders
(74) *Attorney, Agent, or Firm* — Cantor Colburn LLP

(57) ABSTRACT

A compound of Formula (I)

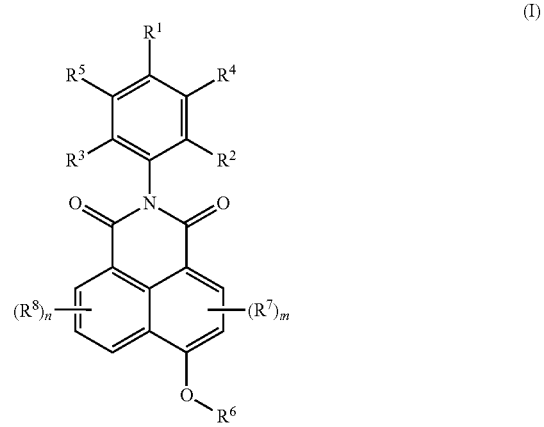

(I)

wherein $R^1$, $R^2$, and $R^3$ are independently at each occurrence hydrogen, a halogen, a cyano functionality, a $C_1$-$C_{20}$ aliphatic functionality, a $C_3$-$C_{10}$ cycloaliphatic functionality or a $C_3$-$C_{20}$ aromatic functionality, with the proviso that $R^2$ and $R^3$ are not hydrogen when $R^1$ is a methyl or hydrogen; $R^4$ and $R^5$ are independently at each occurrence hydrogen, a halogen, a cyano functionality, a $C_1$-$C_{20}$ aliphatic functionality, a $C_3$-$C_{10}$ cycloaliphatic functionality or a $C_3$-$C_{10}$ aromatic functionality; $R^7$ and $R^8$ are independently at each occurrence, a halogen, a cyano functionality, a $C_1$-$C_{20}$ aliphatic functionality, a $C_3$-$C_{10}$ cycloaliphatic functionality or a $C_3$-$C_{10}$ aromatic functionality; $R^6$ is a $C_2$-$C_{20}$ aliphatic functionality, a $C_3$-$C_{10}$ cycloaliphatic functionality or a $C_3$-$C_{20}$ aromatic functionality; and "n" and "m" are each independently integers having a value of 0 to 3.

10 Claims, No Drawings

(56) References Cited

OTHER PUBLICATIONS

Japanese Patent No. 56167383; Publication Date; Dec. 23, 1981; Abstract Only; 1 page.
Japanese Patent No. 59114546; Publication Date; Jul. 2, 1984; Abstract Only; 1 page.
Li et al; "A New Class of High Tg and Organosoluble Polynaphthalimides"; Polymer, Elsevier Science Publishers V. B., GB; vol. 48, No. 11; May 11, 2007; pp. 3082-3089.
Piroux F et al.; "On the Polynaphthalimide Synthesis-Influence of Reaction Conditions"; Polymer, Elsevier Science Publishers B.V., GB; vol. 45. No. 19; Sep. 3, 2004 pp. 6445-6452.
Written Opinion of the International Searching Authority; International Application No. PCT/US2006/044998; International Filing Date: Nov. 20, 2008; Date of Mailing: Jun. 9, 2008; 15 pages.

FLUORESCENT BRIGHTENERS, METHODS OF PREPARATION THEREOF, FLUORESCENT BRIGHTENER COMPOSITIONS, AND METHODS OF PREPARATION AND USES THEREOF

CROSS-REFERENCE TO RELATED APPLICATIONS

This application is a division of U.S. patent application Ser. No. 12/561,764, filed Sep. 17, 2009, now U.S. Pat. No. 8,183,310 and U.S. patent application Ser. No. 11/285,336, filed Nov. 21, 2005, now U.S. Pat. No. 7,608,715.

BACKGROUND OF THE INVENTION

This disclosure relates to fluorescent brighteners. More particularly the disclosure relates to fluorescent brighteners, methods of preparing the fluorescent brighteners, compositions comprising the fluorescent brighteners, in particular polymer compositions comprising the fluorescent brighteners, and uses thereof.

Fluorescent brighteners, also known as fluorescent whitening agents, fluorescent whiteners, optical brighteners, and optical whiteners, are additives that alter the visual properties of polymers. Fluorescent brighteners are colorless to weakly colored organic compounds. When in solution, applied to a substrate, or combined with a polymer, they absorb primarily ultraviolet light in the 300 to 400 nanometer (nm) range. Most of the absorbed energy is then re-emitted as visible violet-to-blue fluorescent light in the 400 to 500 nm range. Fluorescent brighteners thus help to mask inherent yellowness in discolored polymers and impart unique, robust color to specialty plastic products.

There are very few fluorescent brighteners exhibiting high Tg values. In addition, many fluorescent brighteners decompose at temperatures commonly used to process polymers. One high Tg fluorescent brightener is 2,2'-(2,5-thiophenediyl)bis[5-(1,1-dimethylethyl)]-benzoxazole, (CAS No. [7128-64-5]) available from Ciba under the trade name UVI-TEX®-OB. Nonetheless, there remains a need in the art for fluorescent brighteners that have a high Tg to enable their use in a wide variety of polymers, especially thermoplastic polymers.

SUMMARY OF THE INVENTION

Disclosed herein is a compound of Formula (I)

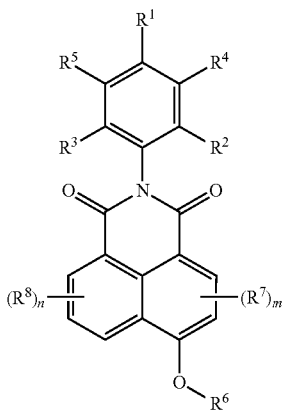

(I)

wherein $R^1$, $R^2$, and $R^3$ are independently at each occurrence hydrogen, a halogen, a cyano functionality, a $C_1$-$C_{20}$ aliphatic functionality, a $C_3$-$C_{10}$ cycloaliphatic functionality, or a $C_3$-$C_{20}$ aromatic functionality, with the proviso that $R^2$ and $R^3$ are not hydrogen when $R^1$ is a methyl or hydrogen; $R^4$ and $R^5$ are independently at each occurrence hydrogen, a halogen, a cyano functionality, a $C_1$-$C_{20}$ aliphatic functionality, a $C_3$-$C_{10}$ cycloaliphatic functionality, or a $C_3$-$C_{10}$ aromatic functionality;

$R^7$ and $R^8$ are independently at each occurrence, a halogen, a cyano functionality, a $C_1$-$C_{20}$ aliphatic functionality, a $C_3$-$C_{10}$ cycloaliphatic functionality, or a $C_3$-$C_{10}$ aromatic functionality; $R^6$ is a $C_2$-$C_{20}$ aliphatic functionality, a $C_3$-$C_{10}$ cycloaliphatic functionality, or a $C_3$-$C_{20}$ aromatic functionality; and "n" and "m" are each independently integers having a value of 0 to 3.

In one embodiment a process for preparing a compound of Formula (I) comprises reacting an anhydride compound of Formula (IV) with an aniline compound of Formula (V)

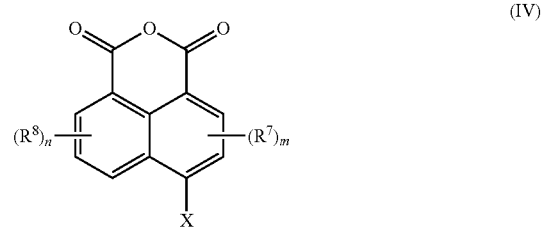

(IV)

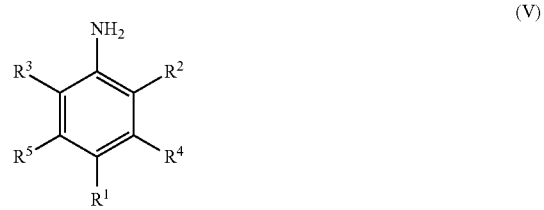

(V)

in the presence of a first solvent to provide a compound of Formula (VI)

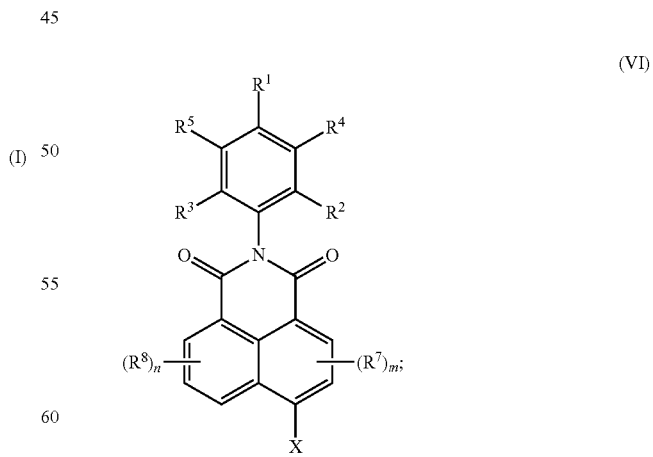

(VI)

reacting the compound of Formula (VI) with a hydroxy compound of Formula (VII)

$R^6$—OH (VII)

in the presence of a base and a second solvent to provide a compound of Formula (I)

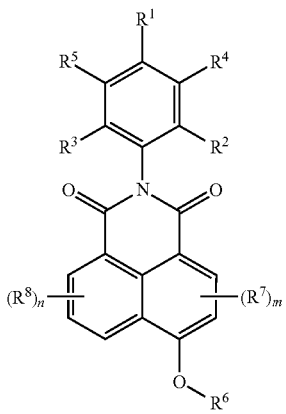

wherein $R^1$, $R^2$, and $R^3$ are independently at each occurrence hydrogen, a halogen, a cyano functionality, a $C_1$-$C_{20}$ aliphatic functionality, a $C_3$-$C_{10}$ cycloaliphatic functionality, or a $C_3$-$C_{20}$ aromatic functionality, with the proviso that $R^2$ and $R^3$ are not hydrogen when $R^1$ is a methyl or hydrogen;

$R^4$ and $R^5$ are independently at each occurrence hydrogen, a halogen, a $C_1$-$C_{20}$ aliphatic functionality, a $C_3$-$C_{10}$ cycloaliphatic functionality, or a $C_3$-$C_{10}$ aromatic functionality;

$R^7$ and $R^8$ are independently at each occurrence a halogen, a $C_1$-$C_{20}$ aliphatic functionality, a $C_3$-$C_{10}$ cycloaliphatic functionality, or a $C_3$-$C_{10}$ aromatic functionality;

$R^6$ is a $C_2$-$C_{20}$ aliphatic functionality, a $C_3$-$C_{10}$ cycloaliphatic functionality, or a $C_3$-$C_{20}$ aromatic functionality;

X is a halogen selected from chlorine, bromine or iodine; and "n" and "m" are each independently integers having a value of 0 to 3.

Also disclosed herein are compositions comprising the compound of Formula (I), methods of making the compositions, and articles comprising the composition comprising the compound of Formula (I).

The above-described and other features are exemplified by the following detailed description.

DETAILED DESCRIPTION OF THE INVENTION

Disclosed herein are compounds having high Tg and that in some embodiments may be used as fluorescent brighteners.

The singular forms "a", "an" and "the" include plural referents unless the context clearly dictates otherwise. All ranges disclosed herein are inclusive of the endpoint and independently combinable (for example ranges of "up to 25 weight (wt.) percent, with 5 wt. percent to 20 wt. percent desired," is inclusive of the endpoints and all intermediate values of the ranges of "5 wt. percent to 25 wt. percent").

The modifier "about" used in connection with a quantity is inclusive of the stated value and has the meaning dictated by the context (for example, includes the degree of error associated with measurement of the particular quantity).

"BPA" is herein defined as bisphenol A, and is also known as 2,2-bis(4-hydroxyphenyl)propane, 4,4'-isopropylidenediphenol, and p,p-BPA.

Unless otherwise specified, the term "cycloaliphatic functionality" designates cyclic aliphatic functionalities having a valence of at least one, and comprising an array of atoms which is cyclic but which is not aromatic. The cycloaliphatic functionality may include heteroatoms such as nitrogen, sulfur, selenium, silicon, and oxygen, or may be composed exclusively of carbon and hydrogen. A "cycloaliphatic functionality" may be linked via the cyclic group or via another group on the cyclic group. For example, a cyclohexylmethyl group ($C_6H_{11}CH_2$—) is a cycloaliphatic functionality that comprises a cyclohexyl ring (the array of atoms which is cyclic but which is not aromatic) and a methylene group (the noncyclic component). A "cycloaliphatic moiety" may further be unsubstituted or substituted, i.e., comprising one or more noncyclic components, including functional groups such as alkyl groups, alkenyl groups, alkynyl groups, haloalkyl groups, halogen(s), conjugated dienyl groups, alcohol groups, ether groups, carboxylic acid groups, acyl groups (for example carboxylic acid derivatives such as esters and amides), amine groups and nitro groups, provided that the functional group(s) do not substantially adversely impact the intended function of the compound. For example, the 4-methylcyclopent-1-yl group is a $C_6$ cycloaliphatic functionality comprising a methyl group, wherein the methyl group is an alkyl functional group. Similarly, the 2-nitrocyclobut-1-yl group is a $C_4$ cycloaliphatic functionality comprising a nitro group, wherein the nitro group is a functional group. Exemplary cycloaliphatic functionalities include cyclopropyl, cyclobutyl, 1,1,4,4-tetramethylcyclobutyl, piperidinyl, 2,2,6,6-tetramethylpiperidinyl, cyclohexyl, and cyclopentyl.

As used herein, the term "aromatic functionality" refers to an array of atoms having a valence of at least one, and comprising at least one aromatic group. The array of atoms comprising the at least one aromatic group may include heteroatoms such as nitrogen, sulfur, selenium, silicon, and oxygen, or may be composed exclusively of carbon and hydrogen. As used herein, the term "aromatic functionality" includes but is not limited to phenyl, pyridyl, furanyl, thienyl, naphthyl, phenylene, and biphenyl functionalities. The aromatic functionality may also include nonaromatic components. For example, a benzyl group is an aromatic functionality that comprises a phenyl ring (the aromatic group) and a methylene group (the nonaromatic component). Similarly a tetrahydronaphthyl functionality is an aromatic functionality comprising an aromatic group ($C_6H_3$) fused to a nonaromatic component —$(CH_2)_4$—. An "aromatic functionality" may further be unsubstituted or substituted with a wide range of functional groups such as alkyl groups, haloalkyl groups, haloaromatic groups, halogens, alcohol groups, ether groups, carboxylic acid groups, acyl groups (for example carboxylic acid derivatives such as esters and amides), amine groups and nitro groups, provided that the functional group(s) do not substantially adversely impact the intended function of the compound. For example, the 4-methylphenyl functionality is a $C_7$ aromatic functionality comprising a methyl group, wherein the methyl group is an alkyl functional group. Similarly, the 2-nitrophenyl group is a $C_6$ aromatic functionality comprising a nitro group, wherein the nitro group is a functional group. Exemplary aromatic functionalities include, but are not limited to phenyl, 4-trifluoromethylphenyl, 4-chloromethylphen-1-yl, 3-trichloromethylphen-1-yl (3-CCl$_3$Ph-), 4-(3-bromoprop-1-yl)phen-1-yl (4-BrCH$_2$CH$_2$CH$_2$Ph-), 4-aminophen-1-yl (4-H$_2$NPh-), 4-hydroxymethylphen-1-yl (4-HOCH$_2$Ph-), 4-methylthiophen-1-yl (4-CH$_3$SPh-), 3-methoxyphen-1-yl, 2-nitromethylphen-1-yl (2-NO$_2$CH$_2$Ph-), and naphthyl.

As used herein the term "aliphatic functionality" refers to an organic functionality having at least one carbon, a valence of at least one, and consisting of a linear or branched array of atoms that is not cyclic. The array of atoms comprising the aliphatic functionality may include heteroatoms such as nitrogen, sulfur, silicon, selenium, and oxygen or may be composed exclusively of carbon and hydrogen. An "aliphatic functionality" may be unsubstituted or substituted with a wide range of functional groups such as alkyl groups, haloalkyl groups, halogens, alcohol groups, ether groups, carboxylic acid groups, acyl groups (for example carboxylic acid derivatives such as esters and amides), amine groups, and nitro groups, provided that the functional group(s) do not substantially adversely impact the intended function of the compound. For example, the 4-methylpent-1-yl is a $C_6$ aliphatic functionality comprising a methyl group, wherein the methyl group is a functional group which is an alkyl group. Similarly, the 4-nitrobut-1-yl group is a $C_4$ aliphatic functionality comprising a nitro group, wherein the nitro group is a functional group. Exemplary aliphatic functionalities include, but are not limited to methyl, ethyl, propyl, isopropyl, butyl, isobutyl, pentyl, isopentyl, trifluoromethyl, bromodifluoromethyl, chlorodifluoromethyl, chloromethyl, trichloromethyl, bromoethyl, 2-hexyl, hexamethylene, hydroxymethyl (—$CH_2OH$), mercaptomethyl (—$CH_2SH$), methylthio (—$SCH_3$), methylthiomethyl (—$CH_2SCH_3$), methoxy, methoxycarbonyl ($CH_3OCO$—), nitromethyl (—$CH_2NO_2$) and thiocarbonyl.

In one embodiment compounds of Formula (I) are disclosed,

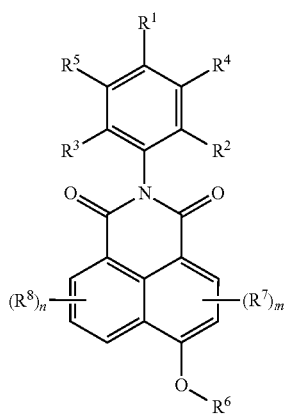

(I)

wherein $R^1$, $R^2$, and $R^3$ are independently at each occurrence hydrogen, a halogen, a cyano functionality, a $C_1$-$C_{20}$ aliphatic functionality, a $C_3$-$C_{10}$ cycloaliphatic functionality, or a $C_3$-$C_{20}$ aromatic functionality, with the proviso that $R^2$ and $R^3$ are not hydrogen when $R^1$ is a methyl or hydrogen; $R^4$ and $R^5$ are independently at each occurrence hydrogen, a halogen, a cyano functionality, a $C_1$-$C_{20}$ aliphatic functionality, a $C_3$-$C_{10}$ cycloaliphatic functionality, or a $C_3$-$C_{10}$ aromatic functionality; $R^7$ and $R^8$ are independently at each occurrence a halogen, a cyano functionality, a $C_1$-$C_{20}$ aliphatic functionality, a $C_3$-$C_{10}$ cycloaliphatic functionality, or a $C_3$-$C_{10}$ aromatic functionality; $R^6$ is a $C_2$-$C_{20}$ aliphatic functionality, a $C_3$-$C_{10}$ cycloaliphatic functionality, or a $C_3$-$C_{20}$ aromatic functionality; and "n" and "m" are each independently integers having a value of 0 to 3.

In one embodiment, $R^1$, $R^4$, and $R^5$ are each hydrogen, $R^2$ and $R^3$ are each a $C_2$-$C_6$ aliphatic functionality that can be the same or different, $R^7$ and $R^8$ are independently at each occurrence a halogen, a cyano functionality, or a $C_1$-$C_6$ aliphatic functionality, and n and m are each 0 to 3.

In a specific embodiment $R^1$, $R^4$, and $R^5$ are hydrogen, $R^2$ and $R^3$ are both a $C_3$ aliphatic functionality, $R^6$ is a $C_2$-$C_4$ aliphatic functionality or a $C_{6-18}$ aromatic functionality and n and m are each 0.

In one embodiment the compound is of Formula (II) or Formula (III)

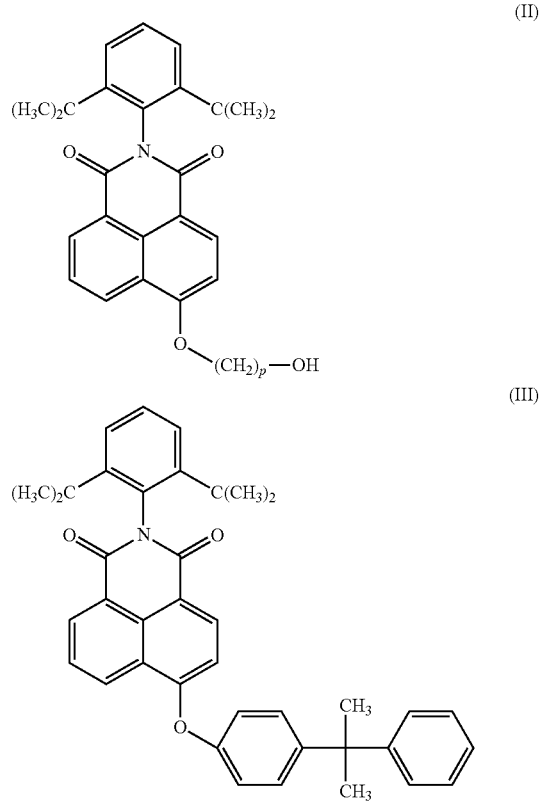

wherein in Formula (II) "p" has a value of 2 to 4. The compound of Formula (II) when "p" is 2 to 4 may be referred to as 2-(2,6-diisopropylphenyl)-6-(2-hydroxyethoxy)-benzo[de]isoquinoline-1,3-dione; 2-(2,6-diisopropylphenyl)-6-(3-hydroxypropoxy)-benzo[de]isoquinoline-1,3-dione and 2-(2,6-diisopropyl-phenyl)-6-(4-hydroxy-butoxy)-benzo[de]isoquinoline-1,3-dione, respectively, and the compound of Formula (III) may be referred to as 2-(2,6-diisopropylphenyl)-6-[4-(1-methyl-1l-phenylethyl)-phenoxy]-benzo[de]isoquinoline-1,3-dione.

In one embodiment a process for making the fluorescent brightener compound of Formula (I) is as follows. An anhydride compound of Formula (IV), wherein X is a halogen, is reacted with an aniline compound of Formula (V)

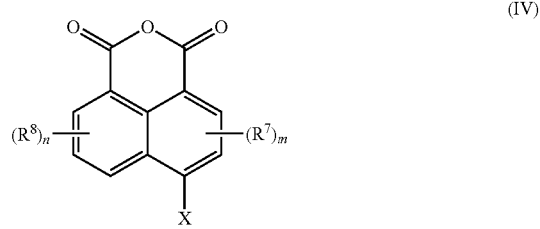

(IV)

-continued

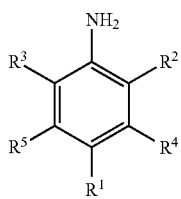
(V)

in the presence of a first solvent to provide a compound of Formula (VI) wherein $R^1, R^2, R^3, R^4, R^5, R^7, R^8$, "n," and "m" have the same meaning as defined above.

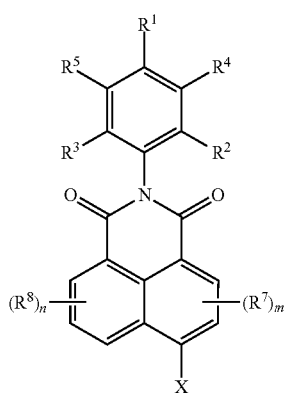
(VI)

Suitable anhydride compounds of Formula (IV) include 4-bromo-1,8-naphthalic anhydride, 4,5-dibromo-1,8-naphthalic anhydride, 2-benzoyl-4-bromo-1,8-naphthalic anhydride, 2-acetyl-4-bromo-1,8-naphthalic anhydride, 2-ethyl-4-bromo-1,8-naphthalic anhydride, 4,6-dibromo-1,8-naphthalic anhydride, and combinations comprising at least one of the foregoing anhydrides.

Suitable aniline compounds of Formula (V) include 2,6-diisopropylaniline, 4-propylaniline, 4-iodo-2-methylaniline, 4-bromo-3-methylaniline, 3-bromo-2,4,6-trimethylaniline, 2-bromo-4-chloroaniline, 4-(1H-imidazol-1-yl)-aniline, and combinations comprising at least one of the foregoing aniline compounds.

The amount of the aniline compound of Formula (V) employed in the reaction can be about 1.0 mole to about 3.0 moles per mole of anhydride compound of Formula (IV) employed. Within this range the amount may be greater than or equal to 1.2 moles, or, more specifically, greater than or equal to about 1.5 moles. Also within this range the amount may be less than or equal to about 2.5 moles, or, more specifically less than or equal to about 2.0 moles.

Specific examples of suitable first solvents that can be employed in the reaction of the anhydride compound of Formula (IV) with the aniline compound of Formula (V) to produce the compound of Formula (VI) include, but are not limited to acetic acid, propionic acid, butanoic acid, ethanol, methanol, propanol, iso-propanol, butanol, iso-butanol, toluene, xylene, dichloromethane, dichloroethane, chloroform, chlorobenzene, ortho-dichlorobenzene, trichlorobenzene, dimethylformamide, diethylacetamide, tetrahydrofuran, dimethylsulfoxide, or combinations of one or more of the foregoing solvents. In one embodiment the solvent employed comprises acetic acid. In certain embodiments the amount of solvent employed in the reaction of the anhydride compound of Formula (IV) with the aniline compound of Formula (V) can be about 10 moles to about 50 moles liters per mole of anhydride compound of Formula (IV). Within this range the amount may be greater than or equal to about 15 moles, or, more specifically, greater than or equal to about 20 moles. Also within this range the amount may be less than or equal to about 40 moles, or, more specifically less than or equal to about 30 moles.

The temperature at which the reaction of the anhydride compound of Formula (IV) with the aniline compound of Formula (V) takes place may be about 80° C. to about 180° C. Within this range the temperature may be greater than or equal to about 90° C., or, more specifically, greater than or equal to about 100° C. Also within this range the temperature may be less than or equal to about 160° C., or, more specifically, less than or equal to about 150° C. The time taken for the reaction of the anhydride compound of Formula (IV) with the aniline compound of Formula (V) can be about 3 hours to about 20 hours. Within this range the time may be greater than or equal to about 5 hours, or, more specifically, greater than or equal to about 10 hours. Also within this range the time may be less than or equal to about 18 hours, or, more specifically, less than or equal to about 15 hours.

The compound of Formula (VI) is reacted with a hydroxy compound of Formula (VII)

$$R^6-OH \quad (VII)$$

wherein $R^6$ is as described above, in the presence of a base and a second solvent to provide a compound of Formula (I) as described above.

Suitable hydroxy compounds of Formula (VII) include, but are not limited to, 1,2-ethylene diol, 1,3-propylene diol, 1,4-butane diol, 4-cumyl phenol, 1,6-hexane diol, 1,7-heptanediol, 1,8-octane diol, 1,4-cyclohexane diol, 1,2-cyclohexane diol, and combinations comprising at least one of the foregoing hydroxy compounds.

The amount of hydroxy compound of Formula (VII) employed in the reaction can be 1 mole to 5 moles per mole of compound of Formula (VI). Within this range the amount may be greater than or equal to about 2 moles, or, more specifically, greater than or equal to about 2.5 moles. Also within this range the amount may be less than or equal to about 4.5 moles, or, more specifically, less than or equal to about 4 moles.

Suitable bases include but are not limited to alkali metal hydroxides, alkali metal carbonates, alkaline earth metal hydroxides, or alkaline earth metal carbonates. Specific alkali metal hydroxides or alkaline earth metal hydroxides include but are not limited to sodium hydroxide, lithium hydroxide, potassium hydroxide, rubidium hydroxide, calcium hydroxide, sodium carbonate, potassium carbonate, and magnesium hydroxide.

In one embodiment a catalyst may be employed in reaction of the compound of Formula (VI) with the hydroxide of Formula (VII). Without being bound to theory it is believed that use of the catalyst will help to increase the speed of the reaction, thereby decreasing reaction time. Suitable catalysts include, but are not limited, to phase transfer catalysts such as tetrabutylammonium bromide, tetrabutylammonium chloride, tetrabutylammonium fluoride trihydrate, tetrabutylammonium hydrogen sulfate, tetrabutylammonium iodide, tetrabutylammonium thiocyanate, tetrabutylammonium tetrafluoroborate, benzyltributylammonium chloride, benzyltriethylammonium chloride, benzyltrimethylammonium bromide, benzyltrimethylammonium chloride, hexadecyltrimethylammonium bromide, hexadecyltrimethylammonium chloride, hexadecyltrimethylammonium hydrogen sulfate, methyltrioctadecylammonium bromide, methyltrioctylammonium bromide, methyltrioctylammonium chloride, tetraethylammonium bromide, tetraethylammonium chloride, tetraethylammonium fluoride dihydrate, tetraethylammonium hexafluorophosphate, tetraethylammonium tetrafluoroborate, tetrahexylammonium hydrogen sulfate, tetramethylammonium bromide, tetramethylammonium chloride, tetraoctylammonium bromide, tetraoctylammonium chloride, polyethylene glycol, hexamethylphosphoramide, tributylmethylphosphonium chloride, tributylmethylphosphonium chloride, hexyltributylphosphonium bromide, tributylmethylammonium chloride, tris[2-(2-methoxyethoxy)ethyl]amine, 4,7,13,16,21,24-hexaoxa-1,10-diazabicyclo[8.8.8]hexacosane, dicyclohexano-24-crown-8, dicyclohexano-18-crown-6,18-Crown-6, dibenzo-24-crown-8, dibenzo-18-crown-6,15-crown-5,1-aza-15-crown-5,12-crown-4, tetrabutylphosphonium bromide, tetrabutylphosphonium chloride and tributylhexadecylphosphonium bromide. Combinations comprising at least one of the foregoing catalysts can be used.

Specific examples of suitable second solvents include but are not limited to toluene, xylene, dichloromethane, dichloroethane, chloroform, chlorobenzene, ortho dichlorobenzene, trichlorobenzene, dimethylformamide, diethylacetamide, tetrahydrofuran, dimethylsulfoxide, or combinations comprising at least one of the foregoing solvents. The amount of second solvent employed in the reaction of compound of Formula (VI) with the hydroxy compound of Formula (VII) can be about 5 moles to about 100 moles per mole of the compound of Formula (VI). Within this range the amount may be greater than or equal to about 10 moles, or, more specifically, greater than or equal to about 20 moles. Also within this range the amount may be less than or equal to about 90 moles, or, more specifically, less than or equal to about 80 moles. In certain embodiments the hydroxy compound of Formula (VII) may be used in addition to or instead of the second solvent. In this embodiment the amount of the hydroxy compound present in the reaction can be 5 moles to 105 moles per mole of the compound of Formula (VI).

The temperature of the reaction of the compound of Formula (VI) with the hydroxy compound of Formula (VII) can be about 80° C. to about 180° C. Within this range the temperature may be greater than or equal to about 90° C., or, more specifically, greater than or equal to about 100° C. Also within this range the temperature may be less than or equal to about 160° C., or, more specifically, less than or equal to about 150° C. The time for the reaction of compound of Formula (VI) with the hydroxy compound of Formula (VII) can be about 4 hours to about 15 hours. Within this range the time may be greater than or equal to about 6 or, more specifically, greater than or equal to about 8 hours. Also within this range the time may be less than or equal to about 14 hours, or, more specifically, less than or equal to about 12 hours.

A polymer composition is also disclosed herein, said composition comprising a polymer and a compound of Formula (I) as described above and or a compound of Formula (VIII)

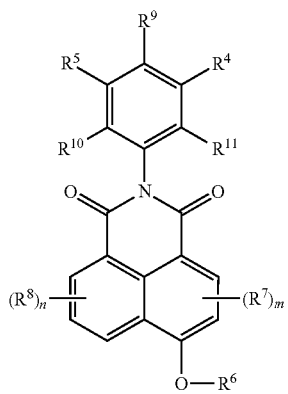

(VIII)

wherein $R^9$, $R^{10}$, and $R^{11}$ are independently at each occurrence hydrogen, a halogen, a cyano functionality, a $C_1$-$C_{20}$ aliphatic functionality, a $C_3$-$C_{10}$ cycloaliphatic functionality or a $C_3$-$C_{20}$ aromatic functionality; $R^4$ and $R^5$ are independently at each occurrence hydrogen, a halogen, a cyano functionality, a $C_1$-$C_{20}$ aliphatic functionality, a $C_3$-$C_{10}$ cycloaliphatic functionality or a $C_3$-$C_{10}$ aromatic functionality; $R^7$ and $R^8$ are independently at each occurrence, a halogen, a cyano functionality, a $C_1$-$C_{20}$ aliphatic functionality, a $C_3$-$C_{10}$ cycloaliphatic functionality or a $C_3$-$C_{10}$ aromatic functionality; $R^6$ is a $C_2$-$C_{20}$ aliphatic functionality, a $C_3$-$C_{10}$ cycloaliphatic functionality or a $C_3$-$C_{20}$ aromatic functionality, "n" and "m" are each independently integers having a value of 1 to 3 and a polymer.

In one embodiment, $R^1$, $R^2$, $R^3$, $R^4$, and $R^5$ are independently at each occurrence hydrogen or a $C_2$-$C_6$ aliphatic functionality, $R^7$ and $R^8$ are independently at each occurrence a halogen, a cyano functionality, or a $C_1$-$C_6$ aliphatic functionality, and n and m are each 0 to 3.

The compounds may be prepared in a similar manner as described for the preparation of the compound of Formula (I).

The compounds of Formulas (I) and (VIII) can have utility as fluorescent brighteners. In one embodiment, a compound that can be used as a fluorescent brightener has an absorption maximum in the 300 to 400 nm range, and an emission maximum in the 400 to 500 nm range, measured in an appropriate solvent, such as dichloromethane. Fluorescent brighteners find utility as an additive to a wide range of materials, including textiles, paper, detergents, and polymers. For example fluorescent brighteners can be used to impart a "whiter-than-white" appearance to polymers pigmented with titanium dioxide; to produce a bluish tinge in clear polymers, masking yellowness; to make lightly colored polymers appear more brilliant; and/or to aid in restoring whiteness to recycled polymers.

One or more of the foregoing effects can be observed with the naked eye, or measured using a tristimulus reflection colorimeter, using the CIELAB color scale, L*, a*, and b*, where L* defines lightness, the a* axis denotes green/red (+/−) and the b* axis defines blue/yellow (+/−). Higher L* values indicate that more light is reflected. Addition of fluorescent brighteners can result in lower b* values. The blue color range occupies the negative (−) side of the b* axis, while the yellow color range occupies the positive side. The lower the b* value, the less yellow color is perceived by the naked eye, and likewise, lower b* values indicate greater perception of whiteness and blue color. Accordingly, when used as fluorescent brighteners, the compounds of Formula (I) decrease the b* value of the composition containing a compound of Formulas (I) relative to the same composition without the compound of Formula (I). In one embodiment the b* value of the composition containing the compound of Formula (I) is decreased by at least 5% of the b* value of the same composition without the compound of Formula (I). Similarly, when used as fluorescent brighteners, the compounds of Formula (VIII) decrease the b* value of the composition containing a compound of Formulas (VIII) relative to the same composition without the compound of Formula (VIII). In one embodiment the b* value of the composition containing the compound of Formula (VIII) is decreased by at least 5% of the b* value of the same composition without the compound of Formula (VIII).

Both of the compounds of Formula (I) and (VIII) (singly or in combination) can be used in the brightening of polymers, especially thermoplastic polymers, for example, polycarbonates, polyesters, polyimides, polyamides, polyetherimides, thermoplastic polyurethanes, epoxide containing polymers, polyvinylchlorides, and others. It is also possible to use combinations comprising one or more of foregoing polymers, for example combinations of polycarbonates and/or polycarbonate copolymers with polyamides, polyesters, other polycarbonates; copolyester-polycarbonates, olefin polymers such as acrylonitrile-butadiene-styrene (ABS), polystyrene, polyethylene; polysiloxanes, polysilanes and/or polysulfones. As used herein, a "combination" is inclusive of all mixtures, blends, and alloys. When the combination is with a non-thermoplastic polymer, in certain embodiments the non-thermoplastic polymer(s) may be present in an amount of less than or equal to 40 weight percent, more specifically less than or equal to 35 weight percent and most specifically less than or equal to about 30 weight percent, based on the total weight of the polymer composition.

When used as an fluorescent brightener in a polymer composition, the compounds of Formula (I) and/or (VIII) can be present in an amount of about 0.05 weight percent to about 20 weight percent, based on the total weight of the composition.

In addition to the polymer, the polymer composition may include various additives ordinarily incorporated in resin compositions of this type, with the proviso that the additives are preferably selected so as to not significantly adversely affect the desired properties of the thermoplastic composition. Mixtures of additives may be used. The amounts of such additives will depend on the desired properties of the composition, and are readily determinable by one of ordinary skill in the art without undue experimentation.

Exemplary additives include such materials as fillers or reinforcing agents, thermal stabilizers, radiation stabilizers, antioxidants, light stabilizers, ultraviolet (UV) light stabilizers, plasticizers, visual effect enhancers, extenders, antistatic agents, catalyst quenchers, mold release agents, flame retardants, infrared shielding agents, whitening agents, blowing agents, anti-drip agents, impact modifiers and processing aids. The different additives that can be incorporated in the polymer compositions of the present invention are typically commonly used and known to those skilled in the art.

Suitable fillers or reinforcing agents include, for example, silicates and silica powders such as aluminum silicate (mullite), synthetic calcium silicate, zirconium silicate, fused silica, crystalline silica graphite, natural silica sand, or the like; boron powders such as boron-nitride powder, boron-silicate powders, or the like; oxides such as $TiO_2$, aluminum oxide, magnesium oxide, or the like; calcium sulfate (as its anhydride, dihydrate or trihydrate); calcium carbonates such as chalk, limestone, marble, synthetic precipitated calcium carbonates, or the like; talc, including fibrous, modular, needle shaped, lamellar talc, or the like; wollastonite; surface-treated wollastonite; glass spheres such as hollow and solid glass spheres, silicate spheres, cenospheres, aluminosilicate (armospheres), or the like; kaolin, including hard kaolin, soft kaolin, calcined kaolin, kaolin comprising various coatings known in the art to facilitate compatibility with the polymeric matrix resin, or the like; single crystal fibers or "whiskers" such as silicon carbide, alumina, boron carbide, iron, nickel, copper, or the like; fibers (including continuous and chopped fibers) such as asbestos, carbon fibers, glass fibers, such as E, A, C, ECR, R, S, D, or NE glasses, or the like; sulfides such as molybdenum sulfide, zinc sulfide or the like; barium compounds such as barium titanate, barium ferrite, barium sulfate, heavy spar, or the like; metals and metal oxides such as particulate or fibrous aluminum, bronze, zinc, copper and nickel or the like; flaked fillers such as glass flakes, flaked silicon carbide, aluminum diboride, aluminum flakes, steel flakes or the like; fibrous fillers, for example short inorganic fibers such as those derived from blends comprising at least one of aluminum silicates, aluminum oxides, magnesium oxides, and calcium sulfate hemihydrate or the like; natural fillers and reinforcements, such as wood flour obtained by pulverizing wood, fibrous products such as cellulose, cotton, sisal, jute, starch, cork flour, lignin, ground nut shells, corn, rice grain husks or the like; organic fillers such as polytetrafluoroethylene; reinforcing organic fibrous fillers formed from organic polymers capable of forming fibers such as poly(ether ketone), polyimide, polybenzoxazole, poly(phenylene sulfide), polyesters, polyethylene, aromatic polyamides, aromatic polyimides, polyetherimides, polytetrafluoroethylene, acrylic resins, poly(vinyl alcohol) or the like; as well as additional fillers and reinforcing agents such as mica, clay, feldspar, flue dust, fillite, quartz, quartzite, perlite, tripoli, diatomaceous earth, carbon black, or the like, or combinations comprising at least one of the foregoing fillers or reinforcing agents.

The fillers and reinforcing agents may be coated with a layer of metallic material to facilitate conductivity, or surface treated with silanes to improve adhesion and dispersion with the polymeric matrix resin. In addition, the reinforcing fillers may be provided in the form of monofilament or multifilament fibers and may be used either alone or in combination with other types of fiber, through, for example, co-weaving or core/sheath, side-by-side, orange-type or matrix and fibril constructions, or by other methods known to one skilled in the art of fiber manufacture. Suitable cowoven structures include, for example, glass fiber-carbon fiber, carbon fiber-aromatic polyimide (aramid) fiber, and aromatic polyimide fiberglass fiber or the like. Fibrous fillers may be supplied in the form of, for example, rovings, woven fibrous reinforcements, such as 0-90 degree fabrics or the like; non-woven fibrous reinforcements such as continuous strand mat, chopped strand mat, tissues, papers and felts or the like; or three-dimensional reinforcements such as braids.

Suitable thermal stabilizer additives include, for example, organophosphites such as triphenyl phosphite, tris-(2,6-dimethylphenyl)phosphite, tris-(mixed mono- and di-nonylphenyl)phosphite; phosphonates such as dimethylbenzene phosphonate, phosphates such as trimethyl phosphate, and combinations comprising at least one of the foregoing heat stabilizers.

Non-limiting examples of antioxidants that can be used in the polymer compositions include tris(2,4-di-tert-butylphenyl)phosphite; 3,9-di(2,4-di-tert-butylphenoxy)-2,4,8,10-tetraoxa-3,9-diphosphaspiro[5.5]undecane; 3,9-di(2,4-dicumylphenoxy)-2,4,8,10-tetraoxa-3,9-diphosphaspiro[5.5] undecane; tris(p-nonylphenyl)phosphite; 2,2',2"-nitrilo [triethyl-tris[3,3',5,5'-tetra-tert-butyl-1,1'-biphenyl-2'-diyl] phosphite]; 3,9-distearyloxy-2,4,8,10-tetraoxa-3,9-diphosphaspiro[5.5]undecane; dilauryl phosphite; 3,9-di[2,6-di-tert-butyl-4-methylphenoxy]-2,4,8,10-tetraoxa-3,9-diphosphaspiro[5.5]undecane; tetrakis(2,4-di-tert-butylphenyl)-4,4'-bis(diphenylene)phosphonite; distearyl pentaerythritol diphosphite; diisodecyl pentaerythritol diphosphite; 2,4,6-tri-tert-butylphenyl-2-butyl-2-ethyl-1,3-propanediol phosphite; tristearyl sorbitol triphosphite; tetrakis(2,4-di-tert-butylphenyl)-4,4'-biphenylene diphosphonite; (2,4,6-tri-tert-butylphenyl)-2-butyl-2-ethyl-1,3-propanediolphosphite; triisodecylphosphite; and combinations comprising at least one of the foregoing antioxidants.

Non-limiting examples of UV stabilizers that can be used include 2-(2'-hydroxyphenyl)-benzotriazoles, for example, the 5'-methyl-; 3',5'-di-tert.-butyl-; 5'-tert-butyl-; 5'-(1,1,3,3-tetramethylbutyl)-; 5-chloro-3',5'-di-tert-butyl-; 5-chloro-3'-tert.-butyl-5'-methyl-; 3'-sec.-butyl-5'-tert.-butyl-; 3'-alpha-methylbenzyl-5'-methyl; 3'-alpha-methylbenzyl-5'-methyl-5-chloro-; 4'-hydroxy-; 4'-methoxy-; 4'-octoxy-; 3',5'-di-tert.- amyl-; 3'-methyl-5'-carbomethoxyethyl-; and 5-chloro-3',5'-di-tert-amyl-derivatives; and Tinuvin® 234 (available from Ciba Specialty Chemicals). Also suitable are the 2,4-bis-(2'-hydroxyphenyl)-6-alkyl-s-triazines, for example, the 6-ethyl-; 6-heptadecyl-; and 6-undecyl-derivatives. 2-Hydroxybenzophenones can also be used, for example, the 4-hydroxy-; 4-methoxy-; 4-octoxy-; 4-decyloxy-; 4-dodecyloxy-; 4-benzyloxy-; 4,2',4'-trihydroxy-; 2,2',4,4'-tetrahydroxy- and 2'-hydroxy-4,4'-dimethoxy-derivatives. 1,3-bis-(2'-Hydroxybenzoyl)-benzenes, for example, 1,3-bis-(2'-hydroxy-4'-hexyloxy-benzoyl)-benzene; 1,3-bis-(2'-hydroxy-4'-octyloxy-benzoyl)-benzene; and 1,3-bis-(2'-hydroxy-4'-dodecyloxybenzoyl)-benzene may also be employed. Esters of optionally substituted benzoic acids, for example, phenylsalicylate; octylphenylsalicylate; dibenzoylresorcin; bis-(4-tert-butylbenzoyl)-resorcin; benzoylresorcin; 3,5-di-tert-butyl-4-hydroxybenzoic acid-2,4-di-tert-butylphenyl ester or -octadecyl ester or -2-methyl-4,6-di-tert-butyl ester may likewise be employed. Acrylates, for example, alpha-cyano-beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or -butyl ester or N-(beta-carbomethoxyvinyl)-2-methyl-indoline may likewise be employed. Oxalic acid diamides, for example, 4,4'-di-octyloxy-oxanilide; 2,2'-di-octyloxy-5,5'-di-tert-butyl-oxanilide; 2,2'-di-dodecyloxy-5,5-di-tert-butyl-oxanilide; 2-ethoxy-2'-ethyl-oxanilide; N,N'-bis-(3-dimethyl-aminopropyl)-oxalamide; 2-ethoxy-5-tert-butyl-2'-ethyloxanilide and the mixture thereof with 2-ethoxy-2'-ethyl-5,4'-di-tert-butyl-oxanilide; or mixtures of ortho- and para-methoxy- as well as of n- and p-ethoxy- disubstituted oxanilides are also suitable as UV stabilizers. Preferably the ultraviolet light stabilizer is 2-(2-hydroxy-5-methylphenyl)-2H-benzotriazole; 2-(2-hydroxy-3,5-di-tert-amylphenyl)-2H-benzotriazole; 2-[2-hydroxy-3,5-di-(alpha,alpha-dimethylbenzyl)phenyl]-2H-benzotriazole; 2-(2-hydroxy-5-tert-octylphenyl)-2H-benzotriazole; 2-hydroxy-4-octyloxybenzophenone; nickel bis(O-ethyl 3,5-di-tert-butyl-4-hydroxybenzylphosphonate); 2,4-dihydroxybenzophenone; 2-(2-hydroxy-3-tert-butyl-5-methylphenyl)-2H-benzotriazole; nickel butylamine complex with 2,2'-thiobis(4-tert-butylphenol); 2-ethoxy-2'-ethyloxanilide; and 2-ethoxy-2'-ethyl-5,5'-ditert-butyloxanilide. Combinations comprising at least one of the foregoing UV stabilizers can be used.

Plasticizers, lubricants, and/or mold release agents additives may also be used. There is considerable overlap among these types of materials, which include, for example, phthalic acid esters such as dioctyl-4,5-epoxy-hexahydrophthalate; tris-(octoxycarbonylethyl)isocyanurate; tristearin; di- or polyfunctional aromatic phosphates such as resorcinol tetraphenyl diphosphate (RDP), the bis(diphenyl)phosphate of hydroquinone and the bis(diphenyl) phosphate of bisphenol-A; poly-alpha-olefins; epoxidized soybean oil; silicones, including silicone oils; esters, for example, fatty acid esters such as alkyl stearyl esters, for example, methyl stearate; stearyl stearate and pentaerythritol tetrastearate, mixtures of methyl stearate and hydrophilic and hydrophobic nonionic surfactants comprising polyethylene glycol polymers, polypropylene glycol polymers, and copolymers thereof, for example, methyl stearate and polyethylene-polypropylene glycol copolymers in a suitable solvent; and waxes such as beeswax, montan wax, paraffin wax. Combinations comprising at least one of the foregoing materials can be used.

Visual effect enhancers, sometimes known as visual effects additives or pigments or colorants may be present in an encapsulated form, a non-encapsulated form, or laminated to a particle comprising polymeric resin. Some non-limiting examples of visual effects additives are aluminum, gold, silver, copper, nickel, titanium, stainless steel, nickel sulfide, cobalt sulfide, manganese sulfide, metal oxides, white mica, black mica, pearl mica, synthetic mica, mica coated with titanium dioxide, metal-coated glass flakes, and colorants, including but not limited, to Perylene Red. The visual effect additive may have a high or low aspect ratio and may comprise greater than 1 facet. Dyes may be employed such as Solvent Blue 35, Solvent Blue 36, Disperse Violet 26, Solvent Green 3, Anaplast Orange LFP, Perylene Red, and Morplas Red 36. Fluorescent dyes may also be employed including, but not limited to, Permanent Pink R (Color Index Pigment Red 181, from Clariant Corporation), Hostasol Red 5B (Color Index #73300, CAS #522-75-8, from Clariant Corporation) and Macrolex Fluorescent Yellow 10GN (Color Index Solvent Yellow 160:1, from Bayer Corporation). Pigments such as titanium dioxide, zinc sulfide, carbon black, cobalt chromate, cobalt titanate, cadmium sulfides, iron oxide, sodium aluminum sulfosilicate, sodium sulfosilicate, chrome antimony titanium rutile, nickel antimony titanium rutile, and zinc oxide may be employed. Combinations comprising at least one of the foregoing visual effects additives can be used. Visual effect additives in encapsulated form usually comprise a visual effect material such as a high aspect ratio material like aluminum flakes encapsulated by a polymer. The encapsulated visual effect additive can have the shape of a bead.

The term "antistatic agent" refers to monomeric, oligomeric, or polymeric materials that can be processed into polymer resins and/or sprayed onto materials or articles to improve conductive properties and overall physical performance. Examples of monomeric antistatic agents include glycerol monostearate, glycerol distearate, glycerol tristearate, ethoxylated amines, primary, secondary and tertiary amines, ethoxylated alcohols, alkyl sulfates, alkylarylsulfates, alkylphosphates, alkylaminesulfates, alkyl sulfonate salts such as sodium stearyl sulfonate, sodium dodecylbenzenesulfonate—quaternary ammonium salts, quaternary ammonium resins, imidazoline derivatives, sorbitan esters, ethanolamides, betaines, and combinations comprising at least one of the foregoing monomeric antistatic agents.

Exemplary polymeric antistatic agents include certain polyesteramides, polyether-polyamide (polyetheramide) block copolymers, polyetheresteramide block copolymers, polyetheresters, or polyurethanes, each containing polyalkylene oxide units that may be polyalkylene glycol moieties, for example, polyethylene glycol, polypropylene glycol and polytetramethylene glycol. Such polymeric antistatic agents are commercially available, such as, for example, Pelestat™ 6321 (Sanyo), Pebax™ H1657 (Atofina), and Irgastat™ P18 and P22 (Ciba-Geigy). Other polymeric materials that may be used as antistatic agents are inherently conducting polymers such as polyaniline (commercially available as PANIPOL®EB from Panipol), polypyrrole and polythiophene (commercially available from Bayer), which retain some of their intrinsic conductivity after melt processing at elevated temperatures. Combinations comprising at least one of the foregoing polymeric antistatic agents can be used. In one embodiment, carbon fibers, carbon nanofibers, carbon nanotubes, carbon black, or any combination of the foregoing may be used in a polymeric resin containing chemical antistatic agents to render the composition electrostatically dissipative.

Non-limiting examples of mold release compositions, combinations of which can be used, include esters of long-chain aliphatic acids and alcohols such as pentaerythritol, guerbet alcohols, long-chain ketones, siloxanes, alpha.-olefin polymers, long-chain alkanes and hydrocarbons having 15 to 600 carbon atoms.

Non-limiting examples of flame retardants that can be used include potassium diphenylsulfone sulfonate, perfluoroalkane sulfonates, the phosphite esters of polyhydric phenols such as resorcinol and bisphenol A, and combinations comprising at least one of the foregoing flame retardants.

The thermoplastic composition may optionally comprise an impact modifier. The impact modifier may be added to the thermoplastic composition in an amount of about 1 percent to about 30 percent by weight, based on the total weight of the composition. Suitable impact modifiers include those comprising one of several different rubbery modifiers such as graft or core shell rubbers or combinations comprising at least one of these modifiers. Impact modifiers are illustrated by acrylic rubber, ASA rubber, diene rubber, organosiloxane rubber, ethylene propylene diene monomer (EPDM) rubber, styrene-butadiene-styrene (SBS) rubber, styrene-ethylene-butadiene-styrene (SEBS) rubber, acrylonitrile-butadiene-styrene (ABS) rubber, methacrylate-butadiene-styrene (MBS) rubber, styrene acrylonitrile copolymer and glycidyl ester impact modifier.

Non-limiting examples of processing aids that can be used include Doverlube® FL-599 (available from Dover Chemical Corporation), Polyoxyter® (available from Polychem Alloy Inc.), Glycolube® P (available from Lonza Chemical Company), pentaerythritol tetrastearate, Metablen® A-3000 (available from Mitsubishi Rayon) and neopentyl glycol dibenzoate.

Radiation stabilizers may also be present in the thermoplastic composition, specifically gamma-radiation stabilizers. Suitable gamma-radiation stabilizers include diols, such as ethylene glycol, propylene glycol, 1,3-propanediol, 1,2-butanediol, 1,4-butanediol, meso-2,3-butanediol, 1,2-pentanediol, 2,3-pentanediol, 1,4-pentanediol and 1,4-hexandiol.; alicyclic alcohols such as 1,2-cyclopentanediol and 1,2-cyclohexanediol; branched acyclic diols such as 2,3-dimethyl-2,3-butanediol(pinacol), and polyols, as well as alkoxy-substituted cyclic or acyclic alkanes. Alkenols with sites of unsaturation are also a useful class of alcohols, examples of which include 4-methyl-4-penten-2-ol, 3-methyl-pentene-3-ol, 2-methyl-4-penten-2-ol, 2,4-dimethyl-4-penten-2-ol, and 9-decen-1-ol. Another class of suitable alcohols is the tertiary alcohols, which have at least one hydroxy substituted tertiary carbon. Examples of these include 2-methyl-2,4-pentanediol (hexylene glycol), 2-phenyl-2-butanol, 3-hydroxy-3-methyl-2-butanone and cycloaliphatic tertiary carbons such as 1-hydroxy-1-methyl-cyclohexane. Another class of suitable alcohols is hydroxymethyl aromatics, which have hydroxy substitution on a saturated carbon attached to an unsaturated carbon in an aromatic ring. The hydroxy substituted saturated carbon may be a methylol group ($-CH_2OH$) or it may be a member of a more complex hydrocarbon group such as would be the case with ($-CR^7HOH$) or ($-CR_2^7OH$) wherein $R^7$ is a complex or a simply hydrocarbon. Specific hydroxy methyl aromatics may be benzhydrol, 1,3-benzenedimethanol, benzyl alcohol, 4-benzyloxy benzyl alcohol and benzyl benzyl alcohol. Specific alcohols are 2-methyl-2,4-pentanediol (also known as hexylene glycol), polyethylene glycol, polypropylene glycol.

Where a foam is desired, a blowing agent may be added to the composition. Suitable blowing agents include for example, low boiling halohydrocarbons; those that generate carbon dioxide; blowing agents that are solid at room temperature and that when heated to temperatures higher than their decomposition temperature, generate gases such as nitrogen, carbon dioxide, ammonia gas or the like, such as azodicarbonamide, metal salts of azodicarbonamide, 4,4' oxybis(benzenesulfonylhydrazide), sodium bicarbonate, ammonium carbonate, or the like, or combinations comprising at least one of the foregoing blowing agents.

Anti-drip agents may also be used, for example a fibril forming or non-fibril forming fluoropolymer such as polytetrafluoroethylene (PTFE). The anti-drip agent may be encapsulated by a rigid copolymer as described above, for example styrene-acrylonitrile copolymer (SAN). PTFE encapsulated in SAN is known as TSAN. Encapsulated fluoropolymers may be made by polymerizing the encapsulating polymer in the presence of the fluoropolymer, for example an aqueous dispersion. TSAN may provide significant advantages over PTFE, in that TSAN may be more readily dispersed in the composition. A suitable TSAN may comprise, for example, about 50 wt. percent PTFE and about 50 wt. percent SAN, based on the total weight of the encapsulated fluoropolymer. The SAN may comprise, for example, about 75 wt. percent styrene and about 25 wt. percent acrylonitrile based on the total weight of the copolymer. Alternatively, the fluoropolymer may be pre-blended in some manner with a second polymer, such as for, example, an aromatic polycarbonate resin or SAN to form an agglomerated material for use as an anti-drip agent. Either method may be used to produce an encapsulated fluoropolymer.

The thermoplastic polymer compositions may be manufactured by methods generally available in the art, for example, in one embodiment, powdered polymer resin and/or other optional components are first blended, for example in a Henschel™ high speed mixer. Other low shear processes including but not limited to hand mixing may also accomplish this blending. The blend is then fed into the throat of a twin-screw extruder via a hopper. Alternatively, one or more of the components may be incorporated into the composition by feeding directly into the extruder at the throat and/or downstream through a sidestuffer. Such additives may also be compounded into a masterbatch with a desired polymeric resin and fed into the extruder. The extruder is generally operated at a temperature higher than that necessary to cause the composition to flow. The extrudate is immediately quenched in a water batch and pelletized. The pellets may be one-fourth inch long (6.35 millimeter) or less as desired. Such pellets may be used for subsequent molding, shaping, or forming.

Shaped, formed, or molded articles comprising the polymer compositions are also provided. The polymer compositions may be molded into useful shaped articles by a variety of means such as injection molding, extrusion, rotational molding, blow molding and thermoforming to form articles such as, for example, computer and business machine housings such as housings for monitors, handheld electronic device housings such as housings for cell phones, electrical connectors, and components of lighting fixtures, ornaments, home appliances, roofs, greenhouses, sun rooms, swimming pool enclosures and automotive applications, for example forward lighting enclosures for car headlamps).

The disclosure is explained in more detail with reference to the following non-limiting Examples.

The reagents used for the present study are laboratory reagent grades and were used without further purifications. Sources for the reagents were as follows: 4-Bromonaphthalic anhydride (Anshan Huifeng Chemical Co. Ltd. China), Acetic acid (S.D. Fine. Chem., Min. assay 99%), Aniline (S.D. Fine. Chem., Min. assay 98%), Diethyl aniline (Aldrich Chemicals, purity 98.00%), Ethylene glycol (S.D. Fine. Chem., Min. assay 98.0%), Propylene glycol, (S.D. Fine chem., India, Min. assay 99%), Butane diol (Aldrich Chemicals, purity 99.00), Sodium Hydroxide (S.D. Fine. Chem., Min. assay 99%), UVITEX® OB (Ciba Specialty Chemicals).

TLC using the eluent system ethyl acetate: n-Hexane (10:90) was used to monitor progress of reactions.

Structure was determined using $^1$H-NMR on a Bruker 300 MHz spectrophotometer.

HPLC data were obtained using Shimadzu HPLC Class-VP instrument and RP Xterra column-$C_{18}$ (a HPLC column manufactured by Waters, USA), 4.6×50 millimeters (mm), 5 micrometers (μm).

TGA analyses were carried out using a TGA 2950 instrument equipped with an auto sampler, and available from TA Instruments.

The UV-VIS spectral characteristics of the fluorescent whiteners (lambda maximum ($\lambda_{max}$) absorption) were measured in dichloromethane in the wavelength region of 300 nm to 800 nm using a double beam UV/VIS Perkin-Elmer Lambda 900 UV/VIS/NIR spectrophotometer.

Fluorescence properties of fluorescent whiteners (lambda maximum ($\lambda_{max}$) emission, were evaluated using Hitachi-F-4500 spectrophotometer. Molded chips of 1 mm thickness containing 0.005% of compound of Formulas (I) or (VIII) along with polycarbonate were used to determine fluorescence properties.

Example 1

This example describes the preparation of 2-(2,6-diisopropyl-phenyl)-6-(2-hydroxyethoxy)-benzo[de]isoquinoline-1,3-dione in two steps.

Step A: Preparation of N-(2,6-diisopropyl phenyl)-4-bromo naphthalimide

A mixture of 4-bromo-1,8-naphthalic anhydride (10 g (grams)), 2,6-diisopropylaniline (6.74 g) and acetic acid (75 milliliters (ml)) was heated under reflux with stirring for 10 (hrs (hours)). The reaction mixture was cooled to room temperature and filtered. The solids obtained were washed first with acetic acid and then with water, and dried at 120° C. for 8 hrs to obtain 13.1 g of the product.

Step B: Preparation of 2-(2,6-diisopropyl-phenyl)-6-(2-hydroxy-ethoxy)-benzo[de]isoquinoline-1,3-dione A mixture of N-(2,6-diisopropyl phenyl)-4-bromo naphthalimide (4.0 grams (g)), sodium hydroxide (0.54 g), and 1,2-ethylene glycol (50 milliliters (ml)) was stirred at 120° C. for 10 hrs. The reaction mixture was cooled to room temperature, 100 ml water was added to the mixture, and the separated solid was filtered, washed with water, and dried at 100° C. for 8 hrs to obtain the crude product in a yield of 2.25 g. The crude product was further purified using column chromatography in an eluent system consisting of ethyl acetate and n-hexane mixture (20:80). $^1$H-NMR: 1.06 δ (d, 12 protons); 2.63 δ (m, 2 proton); 3.92 δ (m, 2 protons); 4.38 δ (triplet, 2 protons); 5.14 δ (Triplet, 1 proton); 7.36 δ (m, 4 protons); 7.88 δ (m, 1 protons); 8.54 δ (Triplet, 2 protons); 8.76 δ (d, 1 protons); Mass (M+): 418.

Example 2

This example describes the preparation of 2-(2,6-diisopropyl-phenyl)-6-(3-hydroxypropoxy)-benzo[de]isoquinoline-1,3-dione.

A mixture of N-(2,6-diisopropylphenyl)-4-bromo naphthalimide (4.0 g, as prepared in Step A of example 1), sodium hydroxide (0.54 g) and 1,3-propane diol (50 ml) was stirred at 120° C. for 10 hrs. The reaction mixture was cooled to room temperature, 100 ml water was added to the mixture, and the separated solid was filtered, washed with water, and dried at 100° C. for 8 hrs to obtain the crude product in a yield of 3.1 g. The crude product was further purified using column chromatography in an eluent system consisting of ethyl acetate and n-hexane mixture (20:80). $^1$H-NMR: 1.18 δ (d, 12 protons); 2.01 δ (s, 1 proton); 2.25 δ (m, 2 protons); 3.96 δ (m, 2 protons); 4.47 δ (m, 2 proton); 7.13 δ (m, 1 protons); 7.34 δ (m, 2 protons); 7.48 δ (m, 1 protons); 7.76 δ (m, 1 protons); 8.65 δ (m, 3 protons).

Example 3

This example describes the preparation of 2-(2,6-diisopropyl-phenyl)-6-(4-hydroxy-butoxy)-benzo[de] isoquinoline-1,3-dione.

A mixture of N-(2,6-diisopropyl phenyl)-4-bromo naphthalimide (4.0 g as prepared in Step A of example 1), sodium hydroxide (0.54 g) and 1,3-butane diol (50 ml) was stirred at 120° C. for 10 hrs. The reaction mixture was cooled to room temperature, 100 ml water was added to the mixture, and the separated solid was filtered, washed with water, and dried at 100° C. for 8 hrs to obtain the crude product in a yield of 3.1 g. The crude product was further purified using column chromatography in an eluent system consisting of ethyl acetate and n-hexane mixture (20:80). $^1$H-NMR: 1.17 δ (m, 12 protons); 1.68 δ (s, 1 proton); 1.90 δ (m, 2 protons); 2.12 δ (m, 2 protons); 2.76 δ (m, 2 proton); 3.82 δ (m, 2 protons); 4.38 δ (m, 2 protons); 7.343 δ (m, 4 protons); 7.77 δ (m, 1 protons); 8.69 δ (m, 3 protons).

Example 4

This example describes the preparation 2-(2,6-diisopropyl-phenyl)-6-[4-(1-methyl-1-phenyl-ethyl)-phenoxy]-benzo[de]isoquinoline-1,3-dione.

A mixture of N-(2,6-diisopropyl phenyl)-4-bromonaphthalimide (4.0 g), potassium hydroxide (0.77 g) and dimethylformamide (30 ml), 18-crown-6 (0.02 g), and p-cumylphenol (3.89 g) was stirred at 50° C. for 6 hours. The reaction mixture was cooled to room temperature, 100 ml water was added to the mixture, and the separated solid was filtered, washed with water and dried at 60° C. for 8 hrs to obtain the crude product in a yield of (5.0 g). The crude product was further purified by carrying out column chromatography (silica gel 60-120 mesh) using ethyl acetate and n-hexane mixture (20:80). H-NMR: 1.18 δ (m, 12 protons); 1.79 δ (s, 6 proton); 2.79 δ (m, 2 protons); 7.34 δ (m, 14 protons); 7.83 δ (m, 1 protons); 8.56 δ (m, 1 protons); 8.79 δ (m, 2 proton).

Example 5

This example describes the preparation of 6-(2-hydroxy-ethoxy)-2-p-tolyl-benzo[de]isoquinoline-1,3-dione.

Step A: Preparation of 6-bromo-2-p-tolyl-benzo[de]isoquinoline-1,3-dione

A mixture of 4-Bromo 1,8 naphthalic anhydride (10 g), p-toluidine (4.08 g) and acetic acid (75 ml) was refluxed with stirring for 10 hours. Water (200 ml) was added at room temperature, the separated solid was filtered, washed with acetic acid followed by water and dried at 100° C. for 8 hours to yield 11.5 g of the product.

Step B: 6-(2-hydroxy-ethoxy)-2-p-tolyl-benzo[de]isoquinoline-1,3-dione

A mixture of 6-bromo-2-p-tolyl-benzo[de]isoquinoline-1,3-dione (4.0 g), sodium hydroxide (0.65 g), and 1,2-ethylene glycol (50 ml) was maintained under reflux with stirring at 120° C. for 10 hrs. The reaction mixture was then cooled to room temperature and water (100 ml) was added to the mixture. The solid that separated out was filtered, washed with water, and dried at 100° C. for 8 hours (Yield=2.71 g). The crude product was purified using 120 ml monochlorobenzene and 0.25 g activated charcoal to obtain pure product weighing 1.32 g. $H^1$-NMR: 2.39 δ (s, 3 protons); 3.92 δ (m, 2 proton); 4.35 δ (t, 2 protons); 5.13 δ (t, 1 proton); 7.22 δ (m, 2 protons); 7.31 δ (m, 3 protons); 7.83 δ (t, 1 proton); 8.44δ (m, 2 protons); 8.68 δ (d, 1 proton).

Example 6

This example describes the preparation of 6-(3-hydroxy-propoxy)-2-phenyl-benzo[de]isoquinoline-1,3-dione.

Step A: Preparation of 6-bromo-2-phenyl-benzo[de]isoquinoline-1,3-dione

A mixture of 4-bromo-1,8-naphthalic anhydride (10 g), aniline (3.54 g) and acetic acid (75 ml) was refluxed with stirring for 10 hrs. The reaction mixture was then cooled to room temperature, whereupon solid separated out. The solid was filtered, washed with water (50 ml) followed by acetic acid (50 ml) and dried at 100° C. for 8 hours (Yield=10.8 gm).

Step B: Preparation of 6-(3-Hydroxy-propoxy)-2-phenyl-benzo[de]isoquinoline-1,3-dione A mixture of 6-bromo-2-phenyl-benzo[de]isoquinoline-1,3-dione (4.0 g), sodium hydroxide (0.67 g) and 1,3-propane diol (50 ml) was maintained with stirring at 120° C. for 10 hrs. The reaction mixture was cooled to room temperature. Water (100 ml) was added to the mixture and solid separated out. The solid was filtered, washed with water, and dried at 100° C. for 8 hours to provide a crude product in a yield of 1.90 g. The crude product was purified using mono chloro benzene (60 ml) and activated charcoal (0.20 g). The weight of the of the purified product obtained was 1.15 g. $^1$H-NMR: 3.93 δ (m, 2 protons); 4.35 δ (m, 1 proton); 2.25 δ (m, 2 protons); 3.96 δ (m, 2 protons); 4.47 δ (m, 2 protons); 7.13 δ (m, 2 protons); 5.14 δ (m, 1 proton); 7.36 δ (m, 3 protons); 7.51 δ (m, 3 protons); 7.84 δ (m, 1 proton); 8.46 δ (m, 2 protons); 8.69 δ (m, 1 proton).

Example 7

This example describes the preparation of 6-(2-hydroxy-ethoxy)-2-phenyl-benzo[de]isoquinoline-1,3-dione.

A mixture of 6-bromo-2-phenyl-benzo[de]isoquinoline-1,3-dione (2.0 g; prepared in step A of Example 5), sodium hydroxide (0.34 g) and 1,2-ethylene glycol (25 ml) was maintained with stirring at 120° C. for 10 hrs. The reaction mixture was cooled to room temperature, water (100 ml) was added to the mixture and solid separated out. The solid was filtered, washed with water, and dried at 100° C. for 8 hours to provide a crude product in a yield of 1.80 g. $^1$H-NMR: 2.07 δ (m, 2 protons); 3.70 δ (m, 2 proton); 4.42 δ (t, 2 protons); 4.68 δ (t, 1 proton); 7.35 δ (m, 3 protons); 7.50 δ (m, 3 protons); 7.83 δ (t, 1 proton); 8.46δ (m, 2 protons); 8.58 δ (d, 1 proton).

A summary of the above results for Examples 1-7 is shown in Table 1 below.

TABLE 1

| Example No. | 4-bromo naphthalimide derivative (g) | Hydroxy compound | Amount of Hydroxy compound | Sodium hydroxide (g) | Purified Yield (g) | Percent Purity (HPLC) |
|---|---|---|---|---|---|---|
| 1 | 4 | 1,2-ethylene glycol | 50 ml | 0.54 | 2.25 | 97.48 |
| 2 | 4 | 1,3-propane diol | 50 ml | 0.54 | 3.10 | 97.83 |
| 3 | 4 | 1,4-butane diol | 50 ml | 0.54 | 2.00 | 93.0 |
| 4 | 4 | p-cumyl phenol | 3.89 g | 0.77[a] g | 5.00[b] | NA |
| 5 | 4 | 1,2-ethylene glycol | 50 ml | 0.65 | 1.32 | 98.03 |
| 6 | 4 | 1,3-propane diol | 50 ml | 0.67 | 1.90 | 97.3 |
| 7 | 2 | 1,2-ethylene glycol | 25 ml | 0.34 | 1.80 | 97.3 |

[a]Potassium hydroxide
[b]Crude yield
NA not available

Characterization of Examples 1-7 and Comparative Example 1 (CE-1)

This example is a comparative study of the properties of a commercially available fluorescence brightener, UVITEX®-OB (Comparative Example 1) and Examples 1-7 above.

The samples were tested for Tg, lambda max absorption, and emission values. Results are shown in Table 2.

TABLE 2

| Example No. | λ max Absorption (nanometers) | λ max Emission (nanometers) | Tg at % weight loss |
|---|---|---|---|
| 1 | 364 | 419.0 | 320 |
| 2 | 366 | 426.0 | 310 |
| 3 | 366 | 421.0 | 350 |
| 4 | 366 | 418.4 | 350 |
| 5 | 364 | 420.0 | 350 |
| 6 | 365 | 429.0 | 370 |
| 7 | 364 | 420.0 | 350 |
| CE-1 | 375 | 437.0 | 310 |

The results provided in Table 2 indicate that the compounds of Formula (I) and Formula (VIII) absorb and emit at relatively lower wavelengths than the commercially available fluorescent brightener UVITEX® OB. Tg at 10 percent weight loss is a measure that indicates the temperature at which the compounds begin to decompose, and refers to the temperature at which the sample has a 10 percent loss in weight compared to the initial amount of sample used for measuring the glass transition temperature (Tg).

While typical embodiments have been set forth for the purpose of illustration, the foregoing descriptions should not be deemed to be a limitation on the scope herein. Accordingly, various modifications, adaptations, and alternatives may occur to one skilled in the art without departing from the spirit and scope herein.

The invention claimed is:

1. A process comprising reacting an anhydride compound of Formula (IV) with an aniline compound of Formula (V)

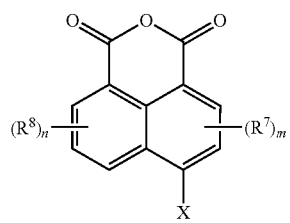

(IV)

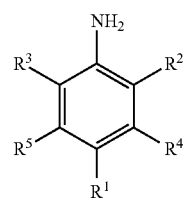

(V)

in the presence of a first solvent to provide a compound of Formula (VI)

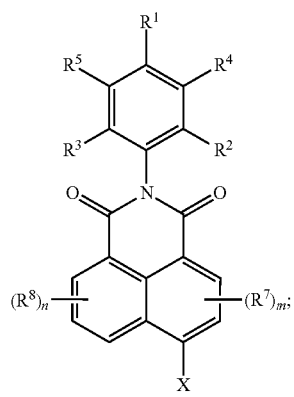

(VI)

wherein $R^1$, $R^4$, and $R^5$ are hydrogen, $R^2$ and $R^3$ are each t-butyl, $R^7$ and $R^8$ are independently at each occurrence a halogen, a cyano functionality, or a $C_1$-$C_6$ functionality, "n" and "m" are each zero, and X is a halogen selected from chlorine or bromine; and reacting the compound of Formula (VI) with a compound of Formula (VII)

$R^6$—OH     (VII)

in the presence of a base and a second solvent to provide a compound of Formula (I)

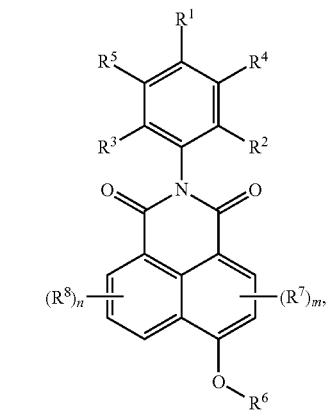

(I)

wherein $R^1$, $R^2$, $R^3$, $R^4$, $R^5$, $R^7$, $R^8$, "n", and "m" have the same meaning as defined above, and $R^6$ is —(CHS$_p$)—OH where p is an integer having a value of 2 to 4, or

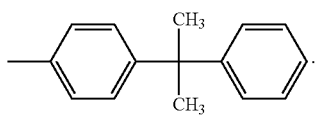

2. The process of claim 1, wherein the reacting of the anhydride compound of Formula (IV) with the aniline compound of Formula (V) is carried out at a temperature of about 80° C. to about 180° C.

3. The process of claim 1, wherein the reacting of a compound of Formula (VI) with a hydroxy compound of Formula (VII) is carried out at a temperature of about 80° C. to about 180° C.

4. The process of claim 1, wherein, X is bromine, the first solvent is acetic acid, and the second solvent is the hydroxy compound of Formula (VII).

5. The process of claim 1, wherein the compound of Formula (VII) is para-cumyl phenol.

6. The process of claim 1, wherein the compound of Formula (VII) is ethylene glycol, propylene glycol, 1,4-butane diol, or a combination thereof.

7. The process of claim 1 wherein the compound of Formula (VII) is ethylene glycol.

8. The process of claim 1, wherein the compound of Formula (VII) is propylene glycol.

9. The process of claim 1, wherein the compound of Formula (VII) is 1,4-butane diol.

10. The process of claim 6, wherein reacting the compound of Formula (VI) with a compound of Formula (VII) further comprises reacting in the presence of a phase transfer catalyst.

* * * * *